(12) United States Patent
Najarian et al.

(10) Patent No.: US 9,974,488 B2
(45) Date of Patent: May 22, 2018

(54) EARLY DETECTION OF HEMODYNAMIC DECOMPENSATION USING TAUT-STRING TRANSFORMATION

(71) Applicant: THE REGENTS OF THE UNIVERSITY OF MICHIGAN, Ann Arbor, MI (US)

(72) Inventors: Kayvan Najarian, Northville, MI (US); Ashwin Belle, Ann Arbor, MI (US); Kevin Ward, Superior Township, MI (US); Harm Derksen, Dexter, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 580 days.

(21) Appl. No.: 14/751,260

(22) Filed: Jun. 26, 2015

(65) Prior Publication Data
US 2015/0374300 A1 Dec. 31, 2015

Related U.S. Application Data

(60) Provisional application No. 62/018,336, filed on Jun. 27, 2014.

(51) Int. Cl.
*G16H 50/20* (2018.01)
*A61B 5/00* (2006.01)

(52) U.S. Cl.
CPC .......... *A61B 5/7253* (2013.01); *G16H 50/20* (2018.01)

(58) Field of Classification Search
CPC ...................................................... G16H 50/20
See application file for complete search history.

(56) References Cited

U.S. PATENT DOCUMENTS

| | | | |
|---|---|---|---|
| 4,680,708 A | 7/1987 | Ambos et al. | |
| 5,025,794 A * | 6/1991 | Albert ................... | A61B 5/044 600/509 |
| 5,655,540 A * | 8/1997 | Seegobin ........... | A61B 5/04525 600/515 |
| 6,493,566 B1 | 12/2002 | Ruchti et al. | |
| 8,062,227 B2 | 11/2011 | Cho et al. | |
| 8,458,240 B2 | 6/2013 | Brown et al. | |
| 9,420,956 B2 * | 8/2016 | Gopalakrishnan . | A61B 5/02405 |
| 2005/0222508 A1 | 10/2005 | Moreno et al. | |
| 2008/0177195 A1 | 7/2008 | Armitstead | |

(Continued)

OTHER PUBLICATIONS

Dumbgen, et al, "Extensions of smoothing via taut strings" Electronic Journal of Statistics vol. 3 (2009) 41-75 (Year: 2009).*

(Continued)

*Primary Examiner* — Neal Sereboff
(74) *Attorney, Agent, or Firm* — Marshall, Gerstein & Borun LLP

(57) ABSTRACT

Techniques develop models for classification for physical conditions of a subject based on monitored physiologic signal data. The models for classification are determined from data transformed and feature extracted using a Taut-string transformation and in some instances using a further Stockwell-transformation, applied in parallel or in series. Physical conditions, specifying the state of hemodynamic stability and reflective of the cardiovascular and nervous systems, are thus modeled using these techniques.

19 Claims, 8 Drawing Sheets

(56) References Cited

U.S. PATENT DOCUMENTS

| | | |
|---|---|---|
| 2009/0234410 A1 | 9/2009 | Libbus et al. |
| 2010/0280334 A1 | 11/2010 | Carlson et al. |
| 2011/0319724 A1 | 12/2011 | Cox |
| 2012/0123232 A1 | 5/2012 | Najarian et al. |
| 2012/0245439 A1 | 9/2012 | Andre et al. |
| 2013/0296726 A1 | 11/2013 | Niebauer et al. |

OTHER PUBLICATIONS

Luo et al., A Hierarchical Method for Removal of Baseline Drift from Biomedical Signals: Application in ECG Analysis, The Scientific World Journal, vol. 2013 (2013).

International Search Report and Written Opinion from Application No. PCT/US2015/037882 dated Oct. 5, 2015.

Ansari, et al. "ϵ-Tube Regression: A New Method for Motion Artifact Reduction," 33rd Annual International Conference of the IEEE EMBS, Boston, MA 2736-2739 (2011).

Arawal, et al. "Time-Frequency Filtering with the S-Transform of ECG Signals," Int J Sci and Res Pub 3(2):1-5 (2013).

Ari, et al. "ECG Signal Enhancement Using S-Transform," Computers in Biology and Medicine 43:649-660 (2013).

Arneodo, et al. "Nucleotide composition effects on the long-range correlations in human genes," European Physical Journal B Condensed Matter, 1:259-263 (1998).

Balouchestani, et al. "Robust Low-Power Algorithm for Random Sensing Matrix for Wireless ECG Systems Based on Low Sampling-Rate Approach," J Signal and Info Proc 4:125-131 (2013).

Belle, et al. "An Automated Optimal Engagement and Attention Detection System Using Electrocardiogram," Computational and Mathematical Methods in Medicine, 12 pages (2012).

Bsoul, et al. "Abstract P115: Prediction of Severity for Blood Volume Loss Using ECG Features Based on P, QRS, and T Waves," Circulation. 120(S1):466 (2009).

Choi, et al., "Improved time-frequency representation of multicomponent signals using exponential kernels," Acoustics, Speech and Signal Processing, IEEE Transactions 37:862-871 (1989).

Cohen, "Time-frequency distributions—a review," Proc IEEE, 77:941-981 (1989).

Convertino, et al. "Estimation of individual-specific progression to impending cardiovascular instability using arterial waveforms," Journal of Applied Physiology 115(8):1196-1202 (2013).

Das, et al. "Analysis of ECG Signal Denoising Method Based on S-Transform," IRBM 34:362-370 (2013).

Davies, et al. "Local Extremes, Runs, Strings and Multiresolution," Annals of Stat. 29(1):1-65 (2001).

Dupuis, et al. "Combined detection of respiratory and cardiac rhythm disorders by high-resolution differential cuff pressure measurement," Instrumentation and Measurement, IEEE Transactions 49:498-502 (2000).

Hadjileontiadis, et al. "Separation of discontinuous adventitious sounds from vesicular sounds using a wavelet-based filter," Biomedical Engineering, IEEE Transactions 44:1269-1281 (1997).

Hlawatsch, et al. "Linear and quadratic time-frequency signal representations," Signal Processing Magazine, IEEE, 9:21-67 (1992).

Ji, et al. "Heart Rate Variability Analysis During Central Hypovolemia Using Wavelet Transformation," J. Clin Monitoring and Computing 27(3):289-302 (2013).

Khalil, et al. "Uterine EMG analysis: a dynamic approach for change detection and classification," Biomedical Engineering, IEEE Transactions 47:748-756 (2000).

Kim, et al. "l1 Trend Filtering," Siam Review 51(2):339-360 (2009).

Marrone, et al. "Multiscale analysis of blood pressure signals," Physical Review E, 60:1088 (1999).

Moulton, et al. "Running on empty? The compensatory reserve index," Journal of Trauma and Acute Care Surgery, 75(6):1053-1059 (2013).

Petrosian, et al. "Recurrent neural network based prediction of epileptic seizures in intra-and extracranial EEG," Neurocomputing 30:201-218 (2000).

Ryan, et al. "Advanced technology development for remote triage applications in bleeding combat casualities," US Army Med Dep J. 61-72 (2011).

Shevade, et al. "Improvements to the SMO Algorithm for SVM Regression," IEEE Transactions on Neural Networks (1999).

Stockwell, et al. "Localization of the complex spectrum: the S transform," Signal Processing, IEEE Transactions 44:998-1001 (1996).

Van Sickle, et al. "A Sensitive Shock Index for Real-Time Patient Assessment During Simulated Hemmorrhage," Aviation, space, and environmental medicine, 84(9):907-912 (2013).

Wo, et al. "Unreliability of blood pressure and heart rate to evaluate cardiac output in emergency resuscitation and critical illness," Crit Car Med 21:218-223 (1993).

Zajtchuk, et al. Battlefield trauma care: focus on advanced technology, Mil Med 160:1-7 (1995).

Zhao, et al. "The use of cone-shaped kernels for generalized time-frequency representations of nonstationary signals," Acoustics, Speech and Signal Processing, IEEE Transactions, 38:1084-1091 (1990).

International Preliminary Report on Patentability from Application No. PCT/US2015/037882 dated Dec. 17, 2016.

* cited by examiner

EARLY DETECTION OF HEMODYNAMIC DECOMPENSATION USING TAUT-STRING TRANSFORMATION

CROSS-REFERENCE TO RELATED APPLICATIONS

This application claims the priority benefit under 35 U.S.C. § 119(e) of U.S. Provisional Patent Application No. 62/018,336, filed Jun. 27, 2014, the disclosure of which is incorporated herein by reference in its entirety.

FIELD OF THE INVENTION

The present disclosure relates to detecting physiologic conditions from electrocardiogram (ECG) signals and, more particularly, early detection of hemodynamic decompensation using a Taut-string and Stockwell transformation on ECG signals.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

Real-time physiologic status monitoring of a hemorrhaging patient, whether military personnel or civilian, can be quite challenging. Starting from the moment of injury and continuing throughout care, care providers would like to monitor patients for hemorrhaging. But such monitoring is difficult in most situations and particularly different in the austere environments where injuries quite often occur. The challenges range from those arising from the environment, to the physical limitations of monitoring devices, to the limited nature of the types of measurements they make. This same problems exist for monitoring a wide array of other patient pathophysiologic conditions, including but not limited to sepsis, cardiogenic shock, congestive heart failure, development of dangerous arrhythmias, stroke, traumatic brain injury, cardiac arrest, myocardial ischemia, etc.

Even current techniques that use standardized monitoring equipment to sample simple vital signs, such as blood pressure, are problematic from an operational standpoint. The size of such equipment, the power requirements, signal fidelity, and robustness are all lacking. And all these limitations affect a care provider's ability to assess and react to a patient before the point of hemodynamic decompensation occurs. Additionally, patients have various abilities to compensate physiologically, which can make detection difficult. Moreover, patient medications can make the use of traditional vital signs to detect early changes in the disease patterns very difficult.

It is desirable to develop new monitoring methodologies and platforms that leverage easily obtainable physiologic signals coupled with the use of advanced bioinformatics techniques to help meet the challenges of monitoring, especially in the austere environments of the battlefield and other pre-hospital locations. In particular, it is desirable to physiologically monitor an injured or ill patient starting at the point of injury or illness.

SUMMARY

In accordance with an example, a method of developing classification models for classifying one or more physical conditions of a subject, the method includes: receiving, from a sensor equipment configured to monitor the subject, raw signal data indicative of a physical state of the subject; applying, in a signal processor, a windowing filter to the raw signal data to create a plurality of windows of the raw signal data; applying, in the signal processor, a pre-processing to each of the plurality of windows of the raw signal data to filter each window by removing spurious noise induced on the raw signal data by the sensor equipment; performing, in the signal processor, a signal decomposition on each window, where the signal decomposition comprises applying a Taut-string transformation to each window to produce Taut-string transformed signal data for each window; performing, in the signal processor, a feature extraction on the Taut-string transformed signal data for each window, wherein the feature extraction is configured to identify one or more features for the raw signal data; and based on the one or more features, developing at least one classification model for classifying the one or more physical conditions of the subject.

In accordance with another example, an apparatus comprises: a memory; and a signal processor coupled to store data on the memory, the signal processor is configured to receive, from a sensor device configured to monitor a subject, raw signal data indicative of a physical state of the subject; apply a windowing filter to the raw signal data to create a plurality of windows of the raw signal data; apply a pre-processing to each of the plurality of windows of the raw signal data to filter each window by removing spurious noise induced on the raw signal data by the sensor equipment; perform a signal decomposition on each window, where the signal decomposition comprises applying a Taut-string transformation to each window to produce Taut-string transformed signal data for each window; perform a feature extraction on the Taut-string transformed signal data for each window, wherein the feature extraction is configured to identify one or more features for the raw signal data; and based on the one or more features, develop at least one classification model for classifying the one or more physical conditions of the subject.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

Figure 1:
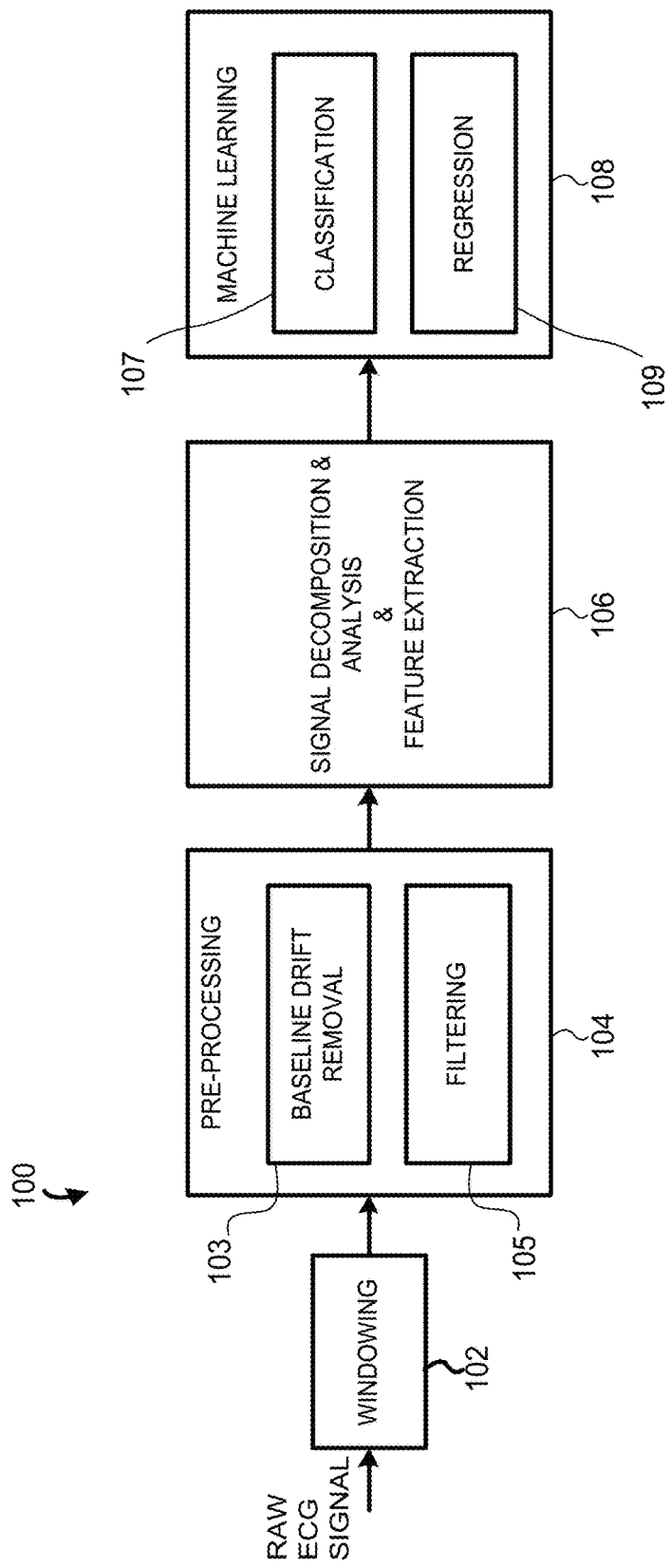
FIG. 1 is a schematic view of a signal analysis configuration having a two-stage signal decomposition and signal analysis stage for extracting features form raw data for machine learning.

The present application proposes techniques for developing models of classification for physical conditions of a subject based on monitored physiologic signal data from that subject, data that is transformed and feature extracted using a Taut-string transformation and in some instances using a further Stockwell-transformation, either in parallel or in series. Once the feature extraction is performed, accurate classification models can be developed to categorize a subject's physical condition. By physical condition, we mean a state of hemodynamic stability that is reflective of the cardiovascular and nervous systems.

In particular examples, a system is used to automatically classify (i.e., categorize) the level hemodynamic compensation or decompensation in response to an illness or injury, by performing an analysis of electrocardiogram (ECG) signals. Other physiologic signals such as the pulse oximetry waveform produced from photoplethysmography (PPG), arterial blood pressure (ABP) waveform, intracranial waveform, electroencelphalogram signals (EEG), and others can also be used in place of the ECG signals, or in combination with ECG signals. The signals may be collected from patients at rest. The signals may be collected from patients performing physical activities, such as through the use of a health activity sensor. Any of one or more of these signals may be collected, in real time or stored, and used as inputs to a classification system employing Taut-string and/or Stockwell transformations as discussed herein. For the example of hemodynamic decompensation severity, the resulting classification can allow care providers to act more quickly to save a subject and ideally avoid possible long-term complications from hemodynamic decompensation. Any of the signals herein may be collected non-invasively or invasively.

Physiologic waveforms such as the ECG are a useful tool in determining the state of the cardiovascular system, but the raw ECG signal as is, is conventionally considered insufficient (without considerable additional processing) for assessing the severity of hemodynamic compensation. Yet, the present disclosure provides signal processing and machine learning techniques that extract valuable hidden insights and patterns from raw signal data in order to extract vital information in predicting physical conditions, such as hemodynamic decompensation. As used herein raw data signals refers to an ability of the present techniques to do feature extraction on collected signal data before any digital filtering is applied to that signal data. There may be analog filtering, in some examples; but preferably there is no digital filtering. It will be appreciated, however, that the present techniques may be applied to raw signals that have been digitally filtered.

The techniques herein may be applied to any number of physical monitoring applications. These applications include: continuous real-time monitoring of critically ill and injured patients in critical care settings with signals collected from bed-side monitors; continuous real-time monitoring of critically ill or injured patients in/out of hospital settings or those at risk for such illness and injuries with ECG signal collected from a portable monitor; continuously monitoring and assessing the cardiovascular and hemodynamic stability of any individual; and real-time monitoring recovery and progress of patient post-operative procedures, both within hospital and out of hospital settings. The human body is networked in a manner that connects critical components of the cardiovascular and neurovascular systems through such pathways as the autonomic nervous system. Because of this connection, illness or injuries that impact on either the cardiovascular system primarily or the nervous system primarily can be detected by close examination of the output of the other system. Variability in signals such as the heart rate as measured by the ECG or vascular tone through measurement of arterial pressure waveforms are capable of providing insight into the health of the connection of the cardiovascular and neurovascular systems since they share looped feedback through systems like the autonomic nervous system. Seemingly diverse disease states like trauma and hemorrhage which impact on the cardiovascular system thus share similar effects on the autonomic nervous system as sepsis, infection, heart failure, cardiogenic shock, cardiac arrest, arrhythmias, pain, and brain injury (ischemic and traumatic). For these reasons, it is believed that early detection of pending severe cardiovascular or central nervous system events, the severity of recognized events, as well as predicting treatment trajectories is possible by monitoring physiologic signals as proposed in this invention.

The techniques use an $l_1$-normalization formulation of Taut-string transformation, and in some examples, and a Stockwell-transform (S-transform), which are both input signal agnostic. That is, these transformations can be performed on any of a variety of signal types, to perform sufficient feature extraction. The present techniques are also application agnostic. That is, the same filtering, decomposition and feature extraction methods can be applied for both medical and non-medical applications, especially those requiring continuous monitoring of physiological data.

The present techniques perform feature extraction on raw physical sensor data, such as health activity data. The features are extracted through a multi stage process by which raw data is pre-processed (filtered to remove noise and interference) and applied to a decomposition and signal analysis stage to extract features. The extracted features are then provided to a learning engine which may include a variety of machine learning methods (such as support vector machines, Random Forrest, Deep Learning, Neural Networks, Regression Trees, etc.) for producing data analysis models to analyze, diagnose, and/or predict one or more physical conditions of a subject. These machine learning methods, such as Support Vector Machines, may be trained with a set of training examples to learn the patterns in the complex patterns and then tested against the data from subjects not included in the training sets. The accuracy and reliability of these machine learning methods may be evaluated using various validation methods including 10-fold Cross Validation method.

FIG. 1 is an example schematic of a system 100 for developing data analysis modules from raw physical sensor data. Initially, raw data is collected from one or more sensors interacting with a subject. The sensors may be attached to the subject, embedded within the subject, a positioned away from and outside of physical contact with the subject. By way of example, the sensors may be selected from various classes of sensors, such as electrical activity-based sensors (such as ECG, EEG, respiratory rate sensors) and physical condition-based sensors (such as pulse oximetry sensors, photoplethysmography sensors, inspiration/expiration sensors, arterial blood pressure sensors, venous blood pressure sensors, impedance sensors, piezoelectric sensors, intracranial pressure sensors, Doppler signal sensors, ultrasound sensors, intracranial pressure sensors, and others).

In the illustrated example, the present techniques are described in reference to the system 100 analyzing raw ECG data and specifically, in reference, to developing models for early detection of hemodynamic decompensation in subjects. The raw signal data is received as new incoming signal data acquired from an ECG monitoring device (not shown). The signal data may be raw signal data to allow for complete pre-processing of signal data by the system 100. Alternatively, the raw data may be provided from a system with some initial preprocessing.

The raw signal data is initially supplied to a windowing stage 102. For example, the system 100 may be trained to process and predict the most useful portions of the signal data using a certain fixed data sized window of the ECG signal. The windowing stage 102 is designed to filter the raw signal data in windows of a particular size that may be buffered and analyzed as discrete blocks of data. For example, as raw signal data is continuously acquired, 20 second intervals of the raw signal data may be separately buffered and sent to the processing algorithm. The windowing stage 102 may apply a certain window size (e.g., anywhere between 10 s to 60 s) when filtering the signal data. The stage 102 may filter the data into immediately adjacent windows, overlapping windows, or spaced apart windows. In this way, generally speaking, there are two variables to the windowing technique.

The first variable is the window size, e.g., 20 seconds of the ECG signal at a time. The window size can vary depending on the type of quantitative analysis to be performed by the system 100. Moreover this window size can be controlled by the system 100 to vary depending on the output of the remaining stages, in a closed loop control configuration, for example.

The second variable is the overlapping nature of the windows, which also includes the amount of spacing between non-overlapping windows. For example, for every 3 seconds of fresh ECG acquisition, the past 17 seconds may be added to it and a new window is formed and sent for analysis. In such an example, there would be an overlap of 17 seconds of data between each successive window. The amount of overlap may be changed depending on how often a new classification is required. Moreover, like the window size, the amount of overlap can be controlled in a closed loop manner, by one or more of the subsequent stages in the system 100.

In some examples, the window size and/or the amount of window overlap may change dynamically, as the system 100 progresses. For example, the amount of overlap could be greater at the beginning of an analysis procedure, to allow the system 100 to determine (e.g., in a recursive manner) an optimum amount of overlap. The amount of overlap may be dynamically shortened, as the system 100 continues operation. In other examples, the amount of overlap may be increased over time. In some examples, the amount of overlap can be made to increase as the system 100 detects an event being experienced by the subject, an event such as hemodynamic decompensation. The same dynamic controls may be applied to changing window size during operation of the system 100, as well.

In the illustrated example, window signal data is buffered at the stage 102 and provided to a pre-processing stage 104. The raw ECG signal as acquired from the physical sensors could inherently contain several artifacts and/or noise that may be detrimental to effective analysis of the signals. Therefore, the pre-processing stage 104 is designed to perform multiple procedures to reduce the effects of these detrimental artifacts. These procedures may be performed sequentially or in parallel.

For example, the stage 104 may perform baseline drift removal, via a stage 103. There are several factors such as loose electrodes, movement of subject etc. that can cause the signal to capture some unwanted trends that shift the signals' baselines unexpectedly. The baseline drift removal is able to remove unwanted spurious signal activity, whether that activity occurs in a continuous manner, in a predictive manner, or more intermittently. For example, the baseline drift removal may apply a best fit model:

Given n points of the ECG signal $(x_1,y_1),(x_2,y_2), \ldots, (x_n,y_n)$, the best fit line associated with these points can be computed as follows:

$$m = \frac{n\left(\sum_1^n xy\right) - \left(\sum_1^n x\right)\left(\sum_1^n y\right)}{n\left(\sum_1^n x^2\right) - \left(\sum_1^n x\right)^2} \quad (1)$$

$$b = \frac{\sum_1^n y - m\left(\sum_1^n x\right)}{n} \quad (2)$$

$$y = mx + b \quad (3)$$

where y is a point on the line, m is the slope of the line and b is the intercept. The computed best fit line for each window is then subtracted from the original signal window to obtain a baseline drift free signal. Other methods can be used to remove the baseline drift. For example, in some examples, baseline drift removal is achieved utilizing an adaptive notch filter and blind source separation (BSS) technique as described in Luo et al., A Hierarchical Method for Removal of Baseline Drift from Biomedical Signals: Application in ECG Analysis, The Scientific World Journal, Vol. 2013 (2013), Article ID 896056. Any linear or nonlinear fitting model may be used to remove baseline drift. Example linear models include logistic regression-based models and moving average models, such as Savitzky-Golay models. Nonlinear models include median filter models, among others. With either model type, highpass filtering, having a preselected cut-off frequency and phase response, may be used. Further, it may also be useful to first detect QRS complexes of an ECG signal and detect and characterize intervals of interest, such as PQ intervals, as a part of baseline drift removal. In any event, it will be appreciated to those skilled in the art that these and other examples of baseline drift removal may performed with the present techniques.

The stage 103, however, may apply any of a variety of different techniques depending on the properties of the signal being analyzed.

The stage 104 may also filter the raw signal data, via a stage 105. An ECG signal can contain noise due to a variety of reasons such as motion artifacts, power line interference, acquisition device quality, etc. Hence, the stage 105 may apply several noise removal filtering techniques. One filtering method is the 'SGolay' filtering method, which stands for Savitzky-Golay filter. This filter is a digital polynomial filter based on least square smoothing mechanism. The SGolay filters are typically used to smooth out a noisy signal with a large frequency span. They perform better than standard averaging FIR filters, although these may be used instead of SGolay filters. Moreover, other types of filters may be used depending on the type of noise to be filter.

The pre-processed raw signal data is then provided to a signal decomposition and analysis stage 106, which identifies features in the received data, features that correlate to analyzing and identifying medical conditions. The size of extracted features may vary. Some features may be window sized, some sub-window sized, while others may be larger than the size of the window. In the examples discussed herein, the features are extracted only from each window and not across multiple windows, i.e., the window size has been set to be large enough to allow for one or more features to be extracted each window. The features may be determined continuously as the raw signal data is buffered and transmitted to the stage 106. Feature extraction may occur based on this windowed signal data alone or by comparing the data with other stored data, such as historical data, collected from previous operations of the system 100 or from other databases, e.g., databases of physical sensor (monitor) data, population data, subject-specific physiological data (age, weight, height, blood pressure and other vital signs, medications, past and current medical/surgical history, mechanisms of injury etc.).

In some examples, the features can be statistical features along the frequency domain, such as, one or more of the mean of frequencies, sum of frequencies, product of frequencies, standard deviation of frequencies, range of frequencies, mean of max frequencies, mean of absolute deviation of frequencies. The statistical-, information-theoretic-, and other types of features may be along the time domain, such as mean, sum, mean of autocovariance, sum of cross-correlation, and $\log_2$ of variance. The statistical features may include various entropy and other nonlinear techniques to measure heart rate complexity, kurtosis, skewness, and others. These features may be determined over data within a window or across data from multiple windows.

After feature extraction on each window, the computed feature set (containing one or more features) from stage 106 is then applied to a machine learning stage 108, which develops diagnostic models, and in some instances, predictive models using a variety of machine learning techniques. These models are also called classification models. In the illustrated example, the learning stage 108 performs two operations, one a classification operation via a stage 107, and another a regression operation via a stage 109. The classification models are designed to provide a physiologic trajectory of the patient in terms of dynamic cardiovascular health. An example is the feed-forward artificial neural network model, also called the multilayer perceptron (MLP), which may be applied to features from stage 106 to provide a numerical index matched to a severity classification depending on the disease process being attempted to be detected. For example, a numerical index may be created that matches a hemodynamic response to hemorrhage or hypovolemia from other causes; and that index may provide several categories of severity (mild, medium, severe, for example). Other examples may include classifications that predict the onset of sepsis or likelihood of sepsis prior to the overt onset of sepsis. The classification models may model any of a number of other physical conditions, including hemodynamic decomposition, trauma, hemorrhage, sepsis, cardiogenic shock, stroke, cardiac arrest, brain injury, pain, arrhythmias, heart failure, infection, level of consciousness, and combinations thereof.

The classification model may be formed as a Random Forest model, the Support Vector Machine (SVM) model, the Rotation Forest model, Rotation Forest, error correction output code model, classification via regression model, decision tree learning algorithms model, clustering algorithms model, pattern recognition algorithms model, feature selection algorithms model, etc.

In the illustrated example, the stage 109 applies a regression technique on the extracted features. The regression model may map the input feature to the output index, which is arranged in a linear scale between 0 and 1. An example regression model includes the support vector regression (SVR) model with radial basis function (RBF) kernels. Other regression models may also be used such as simple linear regression, etc.

The machine learning stage 108 is, therefore, able to develop models that predict (or predict itself) physiological events/complications from the extracted features.

In some examples the stage 108 is also able to produce a health report and/or alarm condition, for example, using the display 426 of signal processing (diagnostic) device 402. The health report and/or alarm condition may be displayed as a web page, mobile alert, tactile alert or alarm (e.g., via a vibrating function of a smartwatch or smartphone), or any other suitable visual and/or tactile display. While in other examples, output data from the stage 108 may be provided to a treatment system, such as therapeutic delivery system for administering a therapeutic treatment to a subject. That delivery system may include an administration system having therapeutic delivery vehicle in communication with a therapeutic treatment processor that controls delivery of the therapeutic treatment in response to received patient status data.

Figure 2:
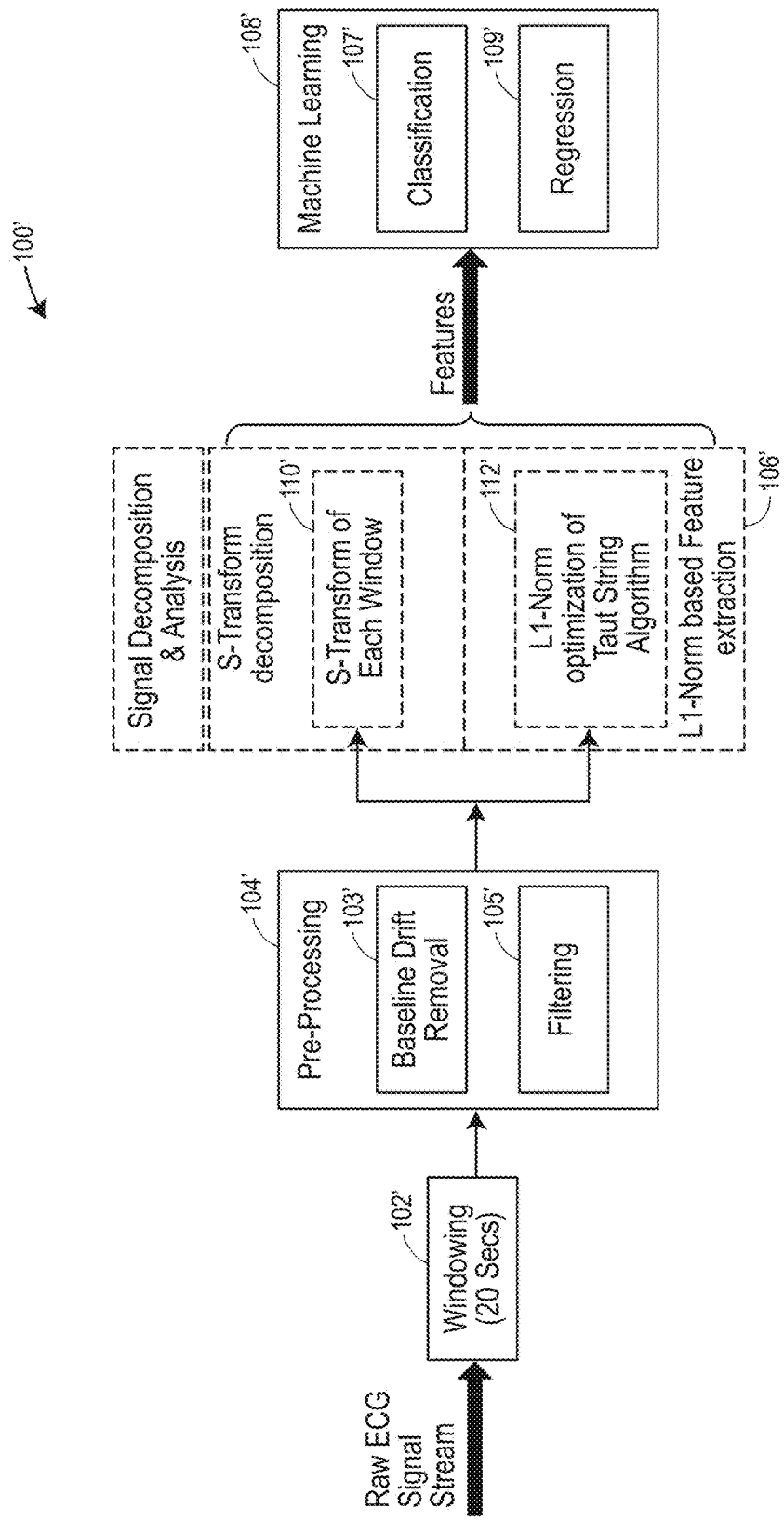
FIG. 2 is a schematic view of the signal analysis configuration of FIG. 1, in accordance with an example, and having a S-transform stage and a Taut-string transformation stage forming the two-stage stage.

FIG. 2 illustrates an example implementation of the system 100 of FIG. 1, labeled system 100' and including a two-stage signal decomposition and analysis stage for the stage 106 (labeled 106'). The stage 106' is configured to perform two transformations of the received pre-processed raw signal data. The first stage is an S-transform stage 110' which performs an S-transform on each window of signal data. This stage 110' thus performs an S-transform decomposition on the received signal data. The second stage is a Taut-string transformation stage 112' which performs a Taut-string feature extraction on the received data.

With respect to the stage 110', a S-transform provides the ability to produce a decomposition of frequency dependent resolution in a hybrid domain of both time and frequency, while entirely retaining the local phase information. In other words, the S-transform not only estimates the local power spectrum, but also the local phase spectrum, which is highly desirable in studying complex physiological signals such as the ECG. This is highly desired in such non-stationary signals such as the ECG.

The stage 112' performs a Taut-string based $l_1$-Norm optimization. For example, using 'R' peaks detected from the QRS complex of each ECG beat, as determined by the stage 112' two derivative signals are produced: (i) the continuous instantaneous heart-rate and (ii) the heart rate variability (HRV). The computed HRV is used to calculate useful features, amongst which are the Taut-string based $l_1$-norm optimization based features. Features extracted from the piecewise linear estimates generated by a Taut-string transformation include:

- Features based on the number of nodes in the window, divided by the number of beats in the window,
- Features based on the number of points of inflection contained in the interval, divided by the number of beats in the window,
- Features based on the total variation between the original signal and the Taut-string estimation, normalized by the number of beats in the window and epsilon.

Apart from the signal decomposition and analysis techniques applied by stages 106/106', the system 100/100' can implement variants of this technology with methods such as Discrete Wavelet Transform (DWT), Dual Tree Complex Wavelet Transform (DTCWT), etc., as discussed below.

In some examples, the block 112' applies a Taut-string transformation directly to the received pre-processed raw signal data from block 104. In other examples, the stage 112' receives, as an input, the output of the S-transformation stage 110, which the stage 112' applies a Taut-string transformation to. The Taut-string transformation allows for de-noising of the incoming raw signal data and high-fidelity compression. Compressed signals can be represented as a series of inflection points connected by a "taut string" rather than a set of thousands of time series data points. The Taut-string transformation may be performed on each window of data and, in that way, in real time. The time to completion of the Taut-string transformation may be linearly related to the size of the dataset, i.e., to the size of the window and the amount of data contained therein.

Conceptually, the Taut-string transformation operates on a data set as if the system were fitting a taut string to data. Each time the string, tautly crossing data, encounters a boundary in the data, the string is turned back in a generally opposite direction. The result is a piecewise liner representation of the data. Each inflection point of the Taut-string fit can be matched to a corresponding peak of the incoming raw ECG data. The transformation is dependent on neighborhood size, such that if too large a neighborhood is used, then the subtler changes in the signal (e.g., P wave peaks or U wave peaks) may be missed. However, too small a neighborhood may introduce artifacts or false positive noise detections.

Figure 4:
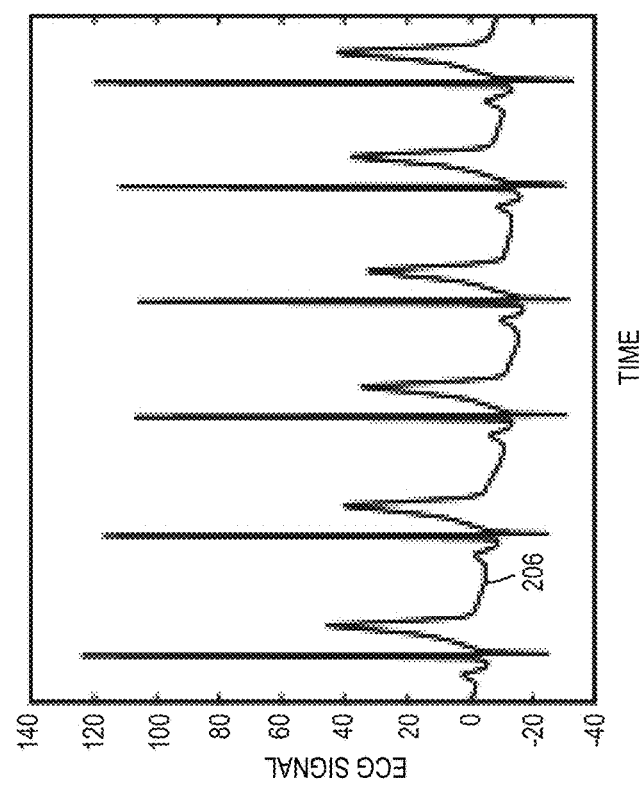
FIG. 4 is a plot illustration of an example Taut-string transformation applied to ECG signal data, in accordance with another example.
Figure 3:
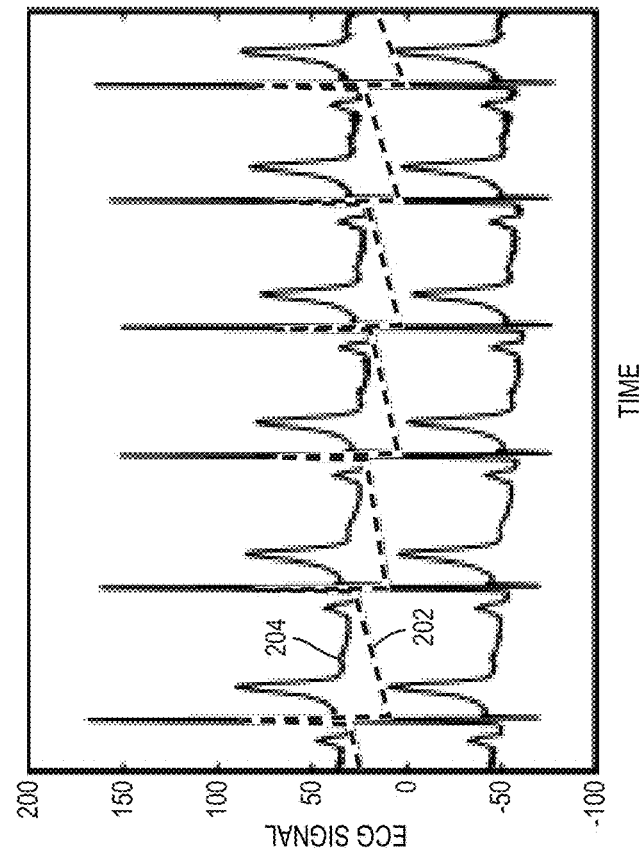
FIG. 3 is a plot illustration of an example Taut-string transformation applied to ECG signal data, in accordance with an example.

FIG. 3 illustrates a Taut-string transformation 202 that has been derived from a larger neighborhood setting used a raw signal ECG data set 204. FIG. 4 illustrates the Taut-string transformation plot 206 from a small neighborhood setting, where the Taut-String plot and the raw signal ECG data set 204 essentially overly, with the Taut-String plot 206 providing a limited amount of smoothing over the data set 204, but retaining a much higher degree of the information from that data set.

Figure 5:
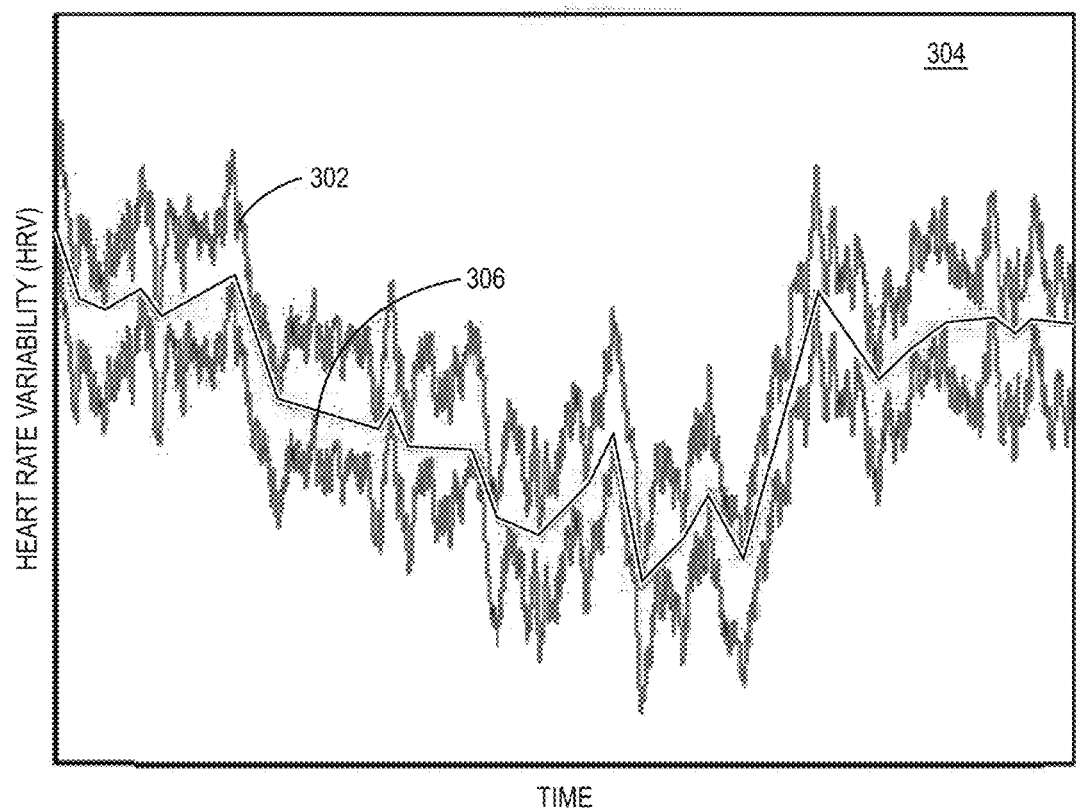
FIG. 5 illustrates an example Taut-string transformation that has been applied to raw data signals of heart rate variability (HRV) from the electrocardiogram data.

The particular Taut-string transformation performed in the example of system 100' is an $l_1$ optimization. The stage 112' may perform a Taut-string transformation in accordance with the following description relating to FIG. 5 which illustrates an example Taut-string transformation that has been applied to raw data signals of heart rate variability (HRV). A plot of HRV data 302, over a window 304, has been transformed to a Taut-string data set 306. For each window, the system 100' has determined the number of line segments that constitute the Taut-string as well as the number of inflection points within that string, whether the inflection points represent a change in slope between ascending and descending for a line segment.

An example implementation of a Taut-string transformation is as follows. Initially, the system defines the difference map (or discrete differentiation) $D: \mathbb{R}^n \to \mathbb{R}^{n-1}$ by $$D(x_1, x_2, \ldots, x_n) = (x_2 - x_1, x_3 - x_2, \ldots, x_n - x_{n-1}).$$

Given a (discrete) function $z \in \mathbb{R}^n$ and a real number $\varepsilon > 0$, the Taut-string method finds a function $x \in \mathbb{R}^n$ for which $\|z - x\|_{2s} \leq \varepsilon$ such that $\|D(x)\|_2$ is minimal. We denote this unique function $x$ by TS $(z, \varepsilon)$. Graphically, the function $x$ can be viewed as a string between $z - \varepsilon$ and $z + \varepsilon$ that is pulled tight (see, FIG. 5). Typically $x$ is a piecewise linear function.

Taut-string techniques first appeared in statistics. If $f \in \mathbb{R}^{n-1}$ is a function (for example a discrete distribution) then one can approximate $f$ by a step function $g$ as follows. First, integrate $f$ to find a function $F \in \mathbb{R}^n$ such that $D(F) = f$ and choose $\varepsilon > 0$. If $G = TS(F, \varepsilon)$ then $g = D(G)$ is a step function that approximates $f$ well, because $\|f - g\|_2$ is minimized under the restriction $\|F - G\|_\infty \leq \varepsilon$.

An example pseudocode for a Taut-string Algorithm is provided below.

```
1:   function TS(z, ε)
2:     n = LENGTH(z)
3:     k_up ← 1
4:     k_down ← 1
5:     z_up[1] ← z[1] + ε
6:     z_down[1] ← z[1] − ε
7:     i_up[1] ← 1
8:     i_down[1] ← 1
9:     j ← 0
10:    for i from 2 to n + 1 do
11:      while k_up > j do
12:        if i = n + 1 then
13:          slope_right ← 0
14:        else
15:          slope_right ← (z[i] + ε − z_up[k_up]) / (i − i_up[k_up])
16:        end if
17:        if k_up = 1 then
18:          slope_left ← 0
19:        else
20:          slope_left ← (z_up[k_up] − z_up[k_up − 1]) / (i_up[k_up] − i_up[k_up − 1])
21:        end if
22:        if slope_right > slope_left then
23:          BREAK
24:        end if
25:        k_up ← k_up − 1
26:      end while
27:      if 1 ≤ n then
28:        k_up ← k_up + 1
29:        i_up[k_up] ← i
30:        z_up[k_up] ← z[i] + ε
31:      end if
32:      while k_down > j do
33:        if i = n +1 then
34:          slope_right ← 0
35:        else
36:          slope_right ← (z[i] − ε − z_down[k_down]) / (i − i_down[k_down])
37:        end if
38:        if k_down = 1 then
39:          slope_left ← 0
40:        else
41:          slope_left ← (z_down[k_down] − z_down[k_down − 1]) / (i_down[k_down] − i_down[k_down − 1])
```

```
42:        end if
43:        if slope_right < slope_left then
44:            BREAK
45:        end if
46:        k_down ← k_down − 1
47:    end while
48:    if i ≤ n then
49:        k_down ← k_down + 1
50:        i_down[k_down] ← i
51:        z_down[k_down] z[i] − ε
52:    end if
53:    while j < k_down − 1 do
54:        if i ≤ n then
55:            slope_right ← (z[i] + ε − z_down[j+1]) / (i − i_down[j+1])
56:        else
57:            slope_right ← 0
58:        end if
59:        if j > 0 then
60:            slope_left ← (z_down[j+1] − z_down[j]) / (i_down[j+1] − i_down[j])
61:        else
62:            slope_left ← 0
63:        end if
64:        if slope_right > slope_left then
65:            BREAK
66:        end if
67:        j ← j + 1
68:        z_up[j] ← z_down[j]
69:        i_up[j] ← i_down[j]
70:        if i ≤ n then
71:            k_up ← k_up + 1
72:            z_up[k_up] ← z[i] + ε
73:            i_up[k_up] ← i
74:        end if
75:    end while
76:    while j < k_up − 1 do
77:        if i ≤ n then
78:            slope_right ← (z[i] − ε − z_up[j+1]) / (i − i_up[j+1])
79:        else
80:            slope_right ← 0
81:        end if
82:        if j > 0 then
83:            slope_left ← (z_up[j+1] − z_up[j]) / (i_up[j+1] − i_up[j])
84:        else
85:            slope_left ← 0
86:        end if
87:        if slope_right < slope_left then
88:            BREAK
89:        end if
90:        j ← j + 1
91:        z_down[j] ← z_up[j]
92:        i_down[j] ← i_up[j]
93:        if i ≤ n then
94:            k_down ← k_down + 1
95:            z_down[k_down] ← z[i] − ε
96:            i_down[k_down] ← i
97:        end if
98:    end while
99:    end for
100:   for i from 1 to i_down[i] do
101:       g[i] = z_down[1]
102:   end for
103:   for j from 1 to k_down − 1 do
104:       for i from i_down[j] 1 to i_down[j+1] do
105:           g[i] = ((i_down[j+1] − i)·z_down[j] + (i − i_down[j])·z_down[j+1]) / (i_down[j+1] − i_down[j])
106:       end for
107:   end for
108:   for i from i_down[k_down] to n do
109:       g[i] = z_down[k_down]
110:   end for
111:   return g
112: end function
```

The Taut-string theory has thus been used, for the first time, for ECG waveform peak detection that allows for significant feature extraction for detection of nonlinear changes in complexity of a received signal. Moreover, in at least some examples, the implementation of the Taut-string algorithm relies upon use of an $l_1$-norm to determine a rectilinear distance from which the ECG (or other signal) is analyzed.

Figure 6A:
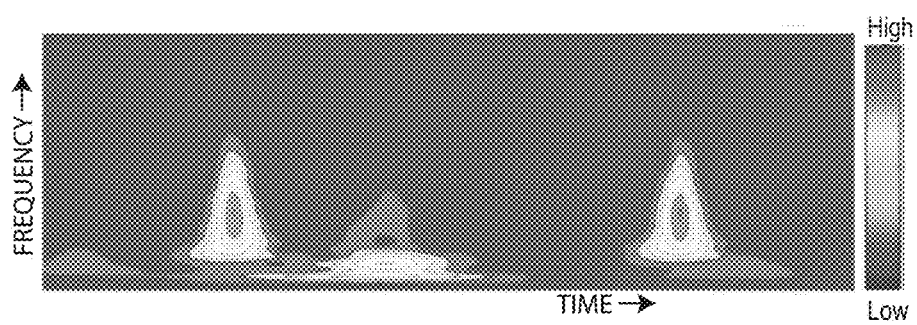
FIGS. 6A-6C illustrate an example S-transform applied to a three-beat window of raw electrocardiogram signal data, in accordance with an example.
Figure 6B:
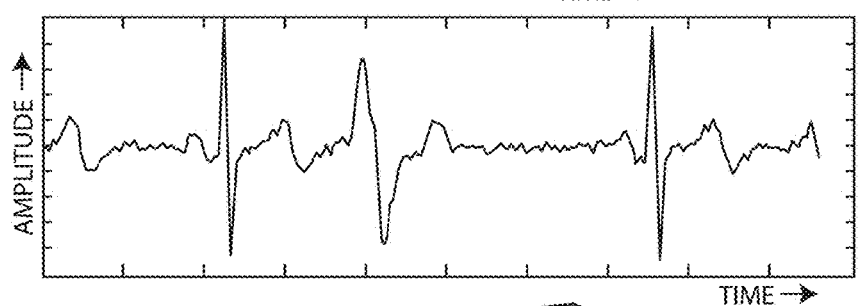
Figure 6C:
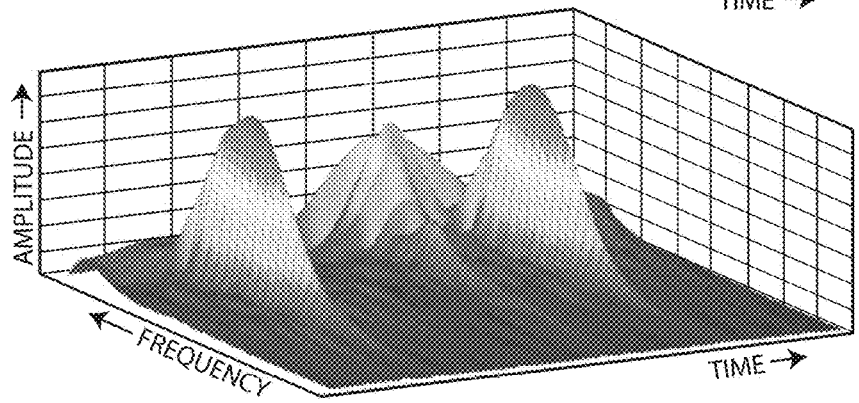

FIGS. 6A-6C illustrate an example of the S-transformation based feature extraction and regression that may be performed by the module 110'. The stage 110' may operate independently from the stage 112', where one or both of the blocks may perform transformations and feature extractions that are provided.

An index called the compensatory reserve index (CRI) has been used before to map the hemodynamic compensation to progression of blood volume loss. The CRI index was produced using central hypovolemia produced by lower body negative pressure (LBNP) levels to model the reduction of central blood volume in the subjects during the simulated hemodynamic compensation. Primarily the CRI index can be computed using LBNP as follows:

$$CRI = 1 - \frac{LBNP(t)}{LBNP_{HDD}}$$

where $LBNP_{HDD}$ is the LBNP level at which the individual enters severe hemodynamic decompensation during the simulation of hypovolemia and LBNP(t) is the LBNP level that the subject is undergoing at time t. The CRI is one of several techniques that may be used to model a dynamic state of physiologic changes associated with a stress such as hypovolemia. It is used in this example to demonstrate the ability the S-Transform and taut-string methods to extract features from the ECG that match the associated hemodynamic changes and their severity over time in response to LBNP, which produces a state of hypovolemia.

In comparison with these studies, with the present techniques a different fundamental signal is being used to estimate severity of decompensation of the subjects. Conventional studies use signals acquired from a finometer, which measures the blood pressure non-invasively on a beat to beat basis. Whereas, the present techniques use an ECG waveform and in a raw signal data format. The ECG waveform may be collected by any known technique, where in one example a wearable armband was used, the SenseWear produced by BodyMedia (http://www.bodymedia.com/).

To utilize such a small footprint portable device for the estimation of hemorrhage severity, the present techniques have been applied to analyze the dynamic and complex nature of the ECG waveform and its subtle morphological changes during hemorrhage. The techniques are able to start with a more detailed raw signal data and perform an extraction that determines more complex features from this raw data. Moreover, the feature extraction may be based on techniques that perform dynamic spectrum analysis in both the time and frequency domain, and in some examples simultaneously, to determine a more informative feature extraction. To analyze the dynamic spectrum or local spectral nature of non-stationary observations, we used techniques that combine time and frequency domain analysis. These include the Cohen class of generalized time-frequency distributions (GTFD), Cone-Kernel distribution, Choi-Williams distribution, as well as the smoothed pseudo Wigner distribution (PWD). In some examples, the stage 110' could perform a single-domain decompensation, such as decomposition and analysis in time-frequency domain using a wavelet transform.

In the illustrated examples, however, the stage 110' applies an S-transform which is distinct from these other analysis techniques in that an S-transform produces decomposition of frequency dependent resolution in the time-frequency domain while entirely retaining the local phase information in the signal data. As a result, the S-transform not only estimates the local power spectrum, but also the local phase spectrum, which is highly desirable in studying complex physiological signals such as the ECG. Although S-transform is similar to continuous wavelet transform in having progressive resolution, unlike wavelet transform, the S-transform retains absolutely referenced phase information and has a frequency invariant amplitude response.

FIGS. 6A-6C illustrates an S-transform instance of a three-beat window of the ECG signal. As can be seen, at any given time, S-transforms represent the smoothed and windowed frequency content of the signal at the time, depicted in different shades from high to low frequency. This results in a rich resolution of information that allows picking up the slight distortion from normal morphology. For instance, as shown in FIG. 6A and FIG. 6C, the distortion in the second beat (i.e., the middle beat) is effectively detected by coefficients of S-transform. Hence S-transform provides an advantageous viewpoint in both time and frequency resolution of an ECG signal data and while highlighting its morphological variation due to decompensation. The S-transform stage 110' may produce a 2-dimensional matrix with rows representing the frequencies and the columns representing time values. The S-transform stage 110' may be tuned to produce a stepwise frequency range with step sizes being 1 Hz and the time interval between samples result in 1 step unit. From here features may be extracted, such as statistical features from the frequency data, such as the To perform the S-transformation, Let h[kT] be the discrete time series signal to be investigated, where k=0,1, . . . , N-1 and T is the time sampling interval. The discrete format of the Fourier transform can be shown as follows:

$$H\left[\frac{n}{NT}\right] = \frac{1}{N}\sum_{k=0}^{N-1}[hT]e^{-\frac{2j\pi nk}{N}} \quad \text{(Eq. 1)}$$

The S transform representation of the time series h[kT] can be represented as follows:

$$S\left[jT, \frac{n}{NT}\right] = \sum_{m=0}^{N-1}H\left[\frac{m+n}{NT}\right]e^{-\frac{2\pi^2 m^2}{n^2}}e^{\frac{2j\pi mj}{N}} \quad n \neq 0 \quad \text{(Eq. 2)}$$

where j,m, and n=0, 1, . . . , N-1.

To descrbove, the incoming ECG waveform is sectioned into 20 second overlapping windows, which are pre-processed, and then decomposed using S-transform in the stage 110'. The output of the S-transform block may be a complex two-dimensional matrix with rows representing the frequencies and the columns represent the time values. Therefore, the block 110' may convert each window into a frequency-time represented matrix.

The extraction of features from the stage 110' output S-transform matrix was performed in two steps. First, the stage 110', may receive the output matrix and reduce the matrix to a single dimension, e.g., but computing certain statistical measures along the frequency dimension, while retaining discreteness in the time dimension as is. In an example, the computed statistical measures along frequency were the mean of frequencies, sum of frequencies, product of frequencies, standard deviation of frequencies, range of frequencies. Second, the stage may determine statistical features along the time domain, mean, sum, mean of auto-covariance, and sum of cross-correlation. Two additional features were determined, in this example, the mean of max frequencies and the mean of absolute deviation of frequencies.

Based on the output of the S-transform stage 110' these features (e.g., statistical, information-theoretic, and/or morphologic) were extracted along with the heart rate computed from the raw ECG signal as an additional feature.

In an example implementation, the stage 110' computed the CRI index for each instance of the feature set for all subjects. The feature sets were then sent through a support vector regression technique, using radial basis functions kernel. The regression may be performed on a per subject basis. Using this framework, for each subject as a test set, the degree of hypovolemia, is determined within the first 24 seconds, following which a new prediction was made every 3 seconds. If desired, predictions could be made more frequently, e.g., every second or as soon as a new beat is detected, but in this implementation, the stage 110' was configured to make predictions once every 3 seconds.

In a testing mode, the objective is to predict the LBNP stage. But because different people will go through different LBNP stages before collapsing, instead of predicting the exact LBNP stage, the present techniques may include normalizing the LBNP stage into an index (CRI). From there train/test models to predict the index which would be the same for all patients regardless of how far in the experiment thy have gone through is determined.

Figure 7:
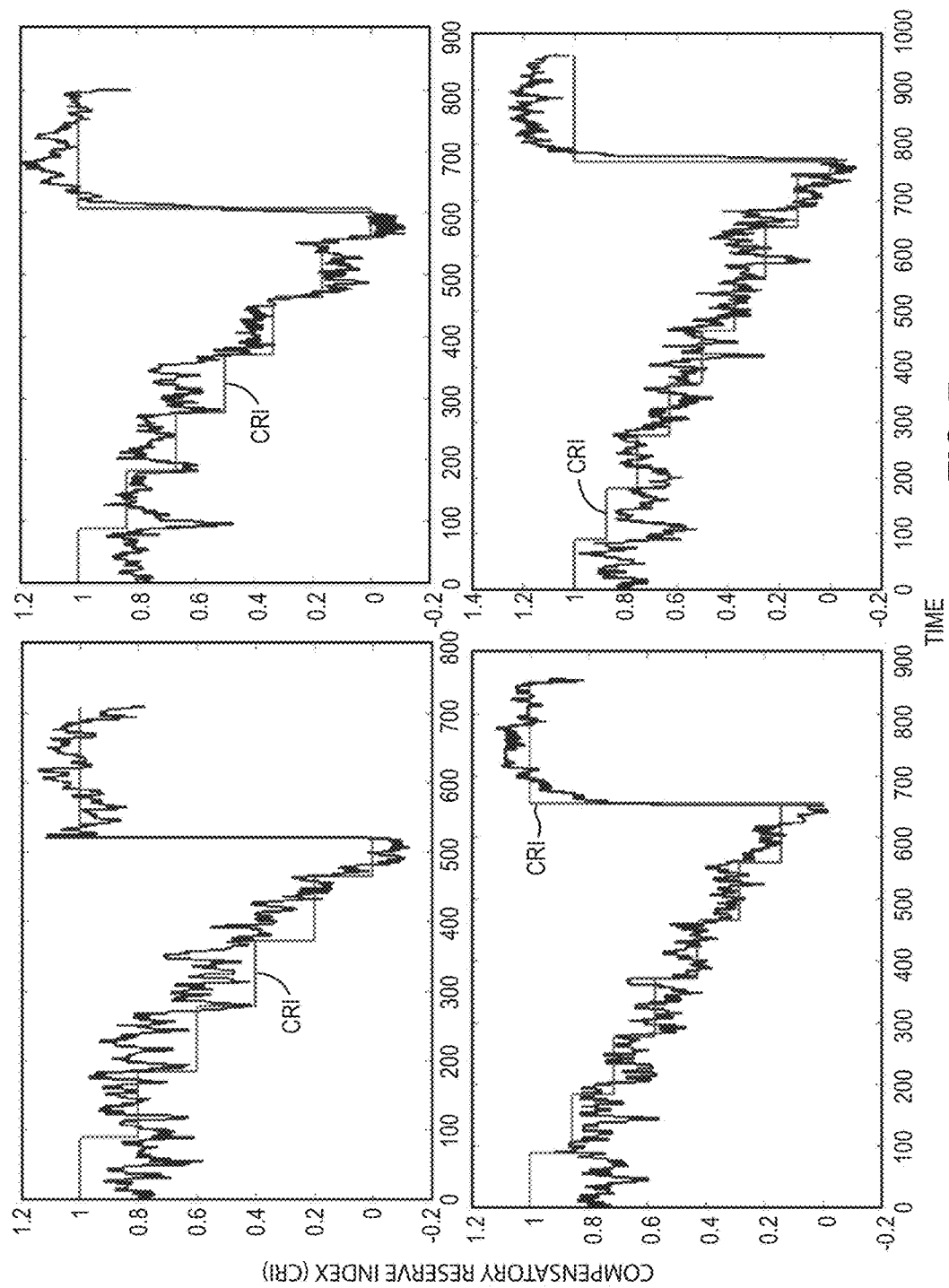
FIG. 7 illustrates a determination of a compensatory reserve index (CRI), in accordance with an example implementation of the schematic of FIG. 1.

FIG. 7 illustrates the estimated CRI value, determined by the stage 110', for 4 out of the 55 subjects against the actual CRI values of these subjects. Each CRI value represents a particular stage of hypovolemia. A CRI value of 1 is when no hypovolemia exists, while each subsequent level is a stepwise increase in the degree of hypovolemia. A CRI value of 0 is when the subject is consider to be highly decompensated and the hypovolemia is treated.

For each of the 55 subjects, the Pearson's correlation coefficient was calculated between the estimated CRI values by the stage 110' and the actual CRI values for that subject. The mean correlation coefficient across all subjects was 0.862 with a standard deviation of 0.072. The mean $r^2$ value across all subjects was 0.928 with a standard deviation of 0.04.

Another set of CRI estimation computed was by omitting the baseline data collected at the beginning of the experiment when there is no LBNP (i.e., omitting operation of the stage 103) and using ECG data only when negative pressure was present including the recovery data at the end after the negative pressure is released. Here the mean correlation coefficient across all subjects was 0.891 with a standard deviation of 0.079. The mean $r^2$ value across all subjects was 0.943 with a standard deviation of 0.045.

With CRI as an extracted feature from the raw signal data, that extracted feature provided to the stage 108 and more particular stage 107 resulted in the stage 107 performing a classification by dividing the CRI values into three classes, wherein CRI estimation greater than 0.6 is considered as adequate compensation, 0.6 to 0.3 is considered as the subject to be moderately compromised, and a CRI value less than 0.3 is considered as onset of cardiovascular and hemodynamic instability. The CRI mapping to the three classes was again performed on a leave-one-subject-out basis. The average accuracy of predicting these classes using the CRI estimation was 80.79%, with a standard deviation of 0.098. The mean sensitivity was 0.78 and mean specificity of 0.93 across all subjects. Thus, this demonstrated effectiveness of the configuration 100' in performing classifications of feature extractions using only the S-transformation.

To perform various feature extractions, the blocks 110' and 112' may be configured to identify global and local peaks and troughs within the raw signal data, as well as spacing distances (or periods) between such elements and inflection points.

Figure 8:
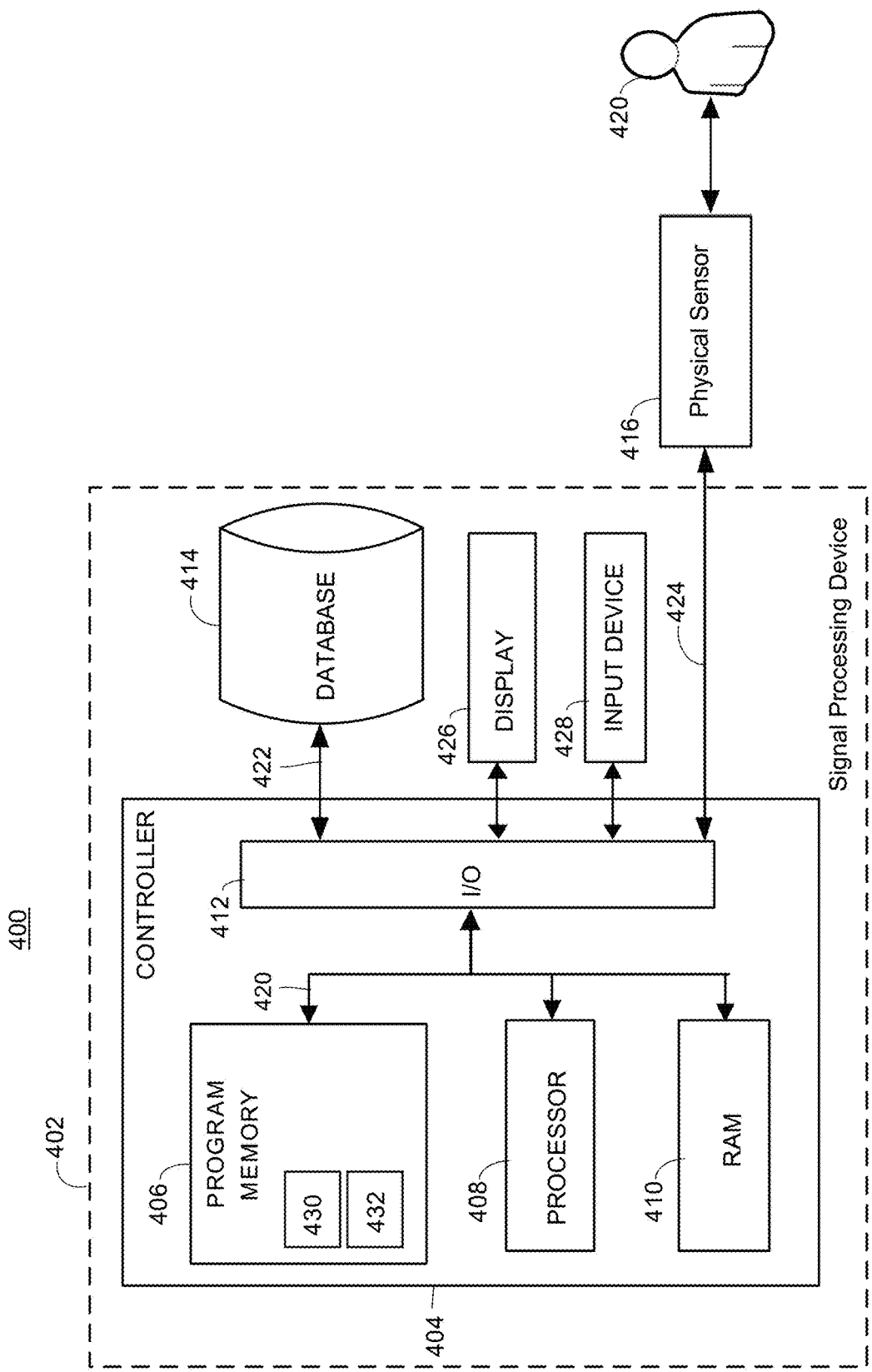
FIG. 8 is a schematic view of an apparatus for developing classification models for classifying one or more physical conditions of a subject and for applying those models to determine a severity of one or more physical conditions of a subject.

FIG. 8 is an example block diagram 400 illustrating the various components used in implementing an example embodiment of the present techniques. A signal processing device 402 (or "signal processor" or "diagnostic device") may be coupled to a patient 420 via one or more physical sensors (including monitors) 416 (e.g., a wearable sensor such as ECG probes) in accordance with executing the functions of the disclosed embodiments. The signal processing device 402 may have a controller 404 operatively connected to the database 414 via a link 422 connected to an input/output (I/O) circuit 412. It should be noted that, while not shown, additional databases may be linked to the controller 404 in a known manner. The controller 404 includes a program memory 406, one or more processors 408 (may be called microcontrollers or a microprocessors), a random-access memory (RAM) 410, and the input/output (I/O) circuit 412, all of which are interconnected via an address/data bus 420. It should be appreciated that although only one processor 408 is shown, the controller 404 may include multiple microprocessors 408. Similarly, the memory of the controller 404 may include multiple RAMs 810 and multiple program memories 406. Although the I/O circuit 412 is shown as a single block, it should be appreciated that the I/O circuit 412 may include a number of different types of I/O circuits. The RAM(s) 410 and the program memories 406 may be implemented as semiconductor memories, magnetically readable memories, and/or optically readable memories, for example. A link 424, which may include one or more wired and/or wireless (Bluetooth, WLAN, etc.) connections, may operatively connect the controller 404 to a physical sensor 416 through the I/O circuit 412. The sensor 416 may be operatively connected to the patient 420.

The program memory 406 and/or the RAM 410 may store various applications (i.e., machine readable instructions) for execution by the processor 408. For example, an operating system 430 may generally control the operation of the signal processing device 402 and provide a user interface to the signal processing device 402 to implement the stages of the configurations 100 and 100' described herein. The program memory 406 and/or the RAM 410 may also store a variety of subroutines 432 for accessing specific functions of the signal processing device 402. By way of example, and without limitation, the subroutines 432 may include, among other things: a subroutine for taking measurements with the sensor 416, a subroutine for filtering measurement (or data) from the sensor 416, a subroutine for performing signal decomposition on raw signal data from the sensor 416, and a subroutine for extracting one or more features of a sensing region from the raw signal data from the sensor 416. The subroutines 432 may also include other subroutines, for example, implementing software keyboard functionality, interfacing with other hardware in the signal processing device 402, etc. The program memory 406 and/or the RAM 410 may further store data related to the configuration and/or operation of the signal processing device 402, and/or related to the operation of the one or more subroutines 432. For example, the data may be data gathered by the sensor 416, data determined and/or calculated by the processor 408, etc. In addition to the controller 404, the signal processing device 402 may include other hardware resources. The signal processing device 402 may also include various types of input/output hardware such as a visual display 426 and input device(s) 428 (e.g., keypad, keyboard, etc.). In an embodiment, the display 426 is touch-sensitive, and may cooperate with a software keyboard routine as one of the software routines 432 to accept user input. It may be advantageous for the signal processing device 402 to communicate with a broader medical treatment network (not shown) through any of a number of known networking devices and techniques (e.g., through a commuter network such as a hospital or clinic intranet, the Internet, etc.). For example, the testing apparatus may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Although depicted as separate entities or components in FIG. 1, it is understood that any or all of the signal processing functionality and/or components of the signal processing device 402 may be combined with a sensor device, such as within an ECG monitoring machine. In this manner, a sensor may both gather data about the patient 420 and process the gathered data to extract one or more features, as discussed further below. Also, although depicted as a single component in FIG. 1, the sensor 416 may include multiple of the same type or different types of sensors. These include but are not limited to arterial blood pressure (ABP) waveforms, electroencephalogram signals, respiratory rate signals, venous pressure signals, impedance signals, photoplethysmography and piezoelectric signals, intracranial pressure signals, Doppler and ultrasound signals, and others.

Figure 9:
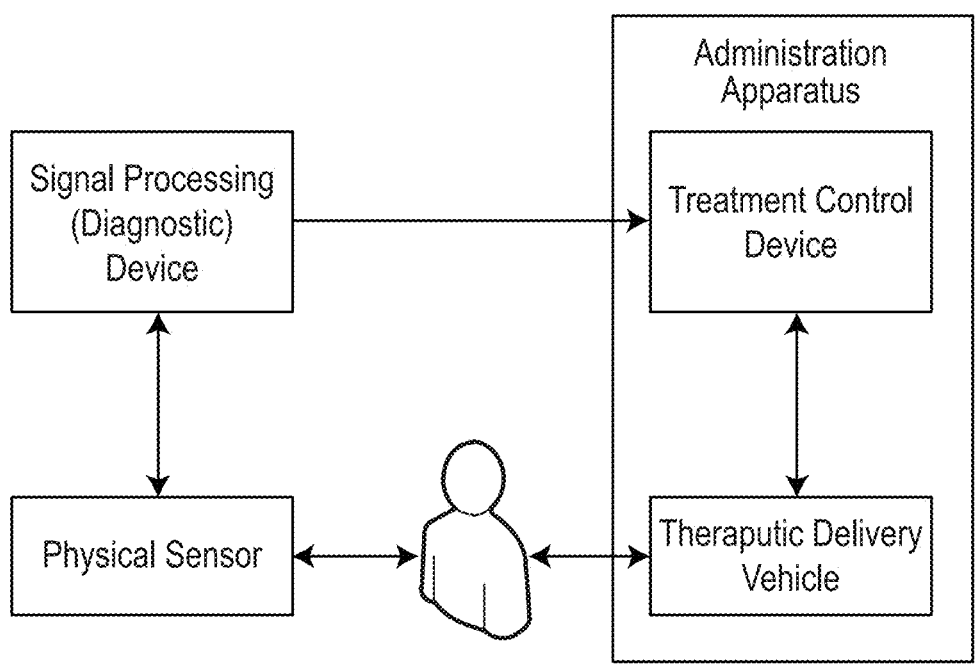
FIG. 9 is a schematic of a therapeutic delivery system for administering a therapeutic treatment to a subject using the apparatus of FIG. 8, in a closed loop manner.

FIG. 9 illustrates an example closed loop system in which a therapeutic treatment may be administered in response to a stored one or more extracted features. A signal processing (diagnostic) device (e.g., device 402) is coupled to a physical sensor (e.g., 416) to monitor a subject and to determine a classification model identifying the severity of one or more physical characters of the subject, in accordance with techniques described. A treatment control device is coupled to therapeutic delivery vehicle. The components are coupled in a closed loop manner, such that the physical sensor monitors the subject and communicates with the signal processing device (part of a diagnostic apparatus) that develops a classification model and/or applies the classification model to identify the severity of one or more physical conditions. That identification may be provided to a treatment administration apparatus that includes a treatment control device, which upon receiving data indicating a sufficient condition for the subject, instructs the therapeutic delivery vehicle to administer a therapeutic treatment to the subject, hopefully to fully address the subject's condition.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. A method of developing classification models for classifying one or more physical conditions of a subject, the method comprises:
   receiving, from a sensor equipment configured to monitor the subject, raw signal data indicative of a physical state of the subject;
   applying, in a signal processor, a windowing filter to the raw signal data to create a plurality of windows of the raw signal data;
   applying, in the signal processor, a pre-processing to each of the plurality of windows of the raw signal data to filter each window by removing spurious noise induced on the raw signal data by the sensor equipment;
   performing, in the signal processor, a signal decomposition on each window, where the signal decomposition comprises applying a Taut-string transformation to each window to produce Taut-string transformed signal data for each window;
   performing, in the signal processor, a feature extraction on the Taut-string transformed signal data for each window, wherein the feature extraction is configured to identify one or more features for the raw signal data; and
   based on the one or more features, developing at least one classification model for classifying the one or more physical conditions of the subject.

2. The method of claim 1, wherein applying the pre-processing comprises:

performing a baseline draft removal on the raw signal data; and
filtering the raw signal data to cancel noise based on motion.

3. The method of claim 1, wherein the one or more extracted features are selected from the group consisting of a mean of frequencies of each window, a sum of frequencies of each window, a product of frequencies of each window, standard deviation of frequencies of each window, range of frequencies of each window, mean of max frequencies of each window, and mean of absolute deviation of frequencies of each window.

4. The method of claim 1, wherein performing the signal decomposition on each window, further comprises:
   applying a Stockwell transformation (S-Transformation) to the raw signal data in each window to produce an S-transformed data set.

5. The method of claim 4, wherein applying a Taut-string transformation to each window comprises applying the Taut-string transformation to the S-transformed data set.

6. The method of claim 4, wherein the raw signal data is electrocardiogram signal data, electroencephalogram data, pulse oximetry waveform data, arterial blood pressure waveform data, venous blood pressure waveform data, intracranial waveform data, or a combination thereof.

7. The method of claim 4, further comprising measuring the raw signal data using an electrocardiogram sensor, a respiratory rate sensor, a pulse oximetry sensor, photoplethysmography sensor, inspiration/expiration sensor, arterial blood pressure sensor, and venous blood pressure sensor, impedance sensor, piezoelectric sensor, a Doppler signal, an ultrasound sensor, or intracranial pressure sensor.

8. The method of claim 1, wherein the classification is of hemodynamic decomposition.

9. The method of claim 1, wherein the classification is of trauma, hemorrhage, sepsis, cardiogenic shock, stroke, cardiac arrest, brain injury, pain, arrhythmias, heart failure, infection, level of consciousness, and/or a combination thereof.

10. A therapeutic delivery system for administering a therapeutic treatment to a subject, the delivery system comprising:
    a diagnostic apparatus implementing the method of claim 1; and
    an administration apparatus comprising a therapeutic delivery mechanism in communication with a processor that controls delivery of the therapeutic treatment in response to a received patient status data from the diagnostic apparatus, the administration apparatus containing the processor and
    (i) coupled to receive the raw signal data, in a closed loop manner,
    (ii) implemented to store the one or more identified features of the raw signal data, and
    (iii) applying the classification model to determine as severity of the one or more physical conditions for the subject
    (iv) implemented to administer the therapeutic treatment, in response to the determined severity of the one or more physical conditions for the subject.

11. An apparatus comprising:
    a memory; and
    a signal processor coupled to store data on the memory, the signal processor is configured to
    receive, from a sensor device configured to monitor a subject, raw signal data indicative of a physical state of the subject;

apply a windowing filter to the raw signal data to create a plurality of windows of the raw signal data;

apply a pre-processing to each of the plurality of windows of the raw signal data to filter each window by removing spurious noise induced on the raw signal data by the sensor equipment;

perform a signal decomposition on each window, where the signal decomposition comprises applying a Taut-string transformation to each window to produce Taut-string transformed signal data for each window;

perform a feature extraction on the Taut-string transformed signal data for each window, wherein the feature extraction is configured to identify one or more features for the raw signal data; and based on the one or more features, develop at least one classification model for classifying the one or more physical conditions of the subject.

12. The apparatus of claim 11, wherein the signal processor is further configured to:

perform a baseline draft removal on the raw signal data; and filter the raw signal data to cancel noise based on motion.

13. The apparatus of claim 11, wherein the one or more extracted features are selected from the group consisting of a mean of frequencies of each window, a sum of frequencies of each window, a product of frequencies of each window, standard deviation of frequencies of each window, range of frequencies of each window, mean of max frequencies of each window, and mean of absolute deviation of frequencies of each window.

14. The apparatus of claim 11, wherein the signal processor is further configured to:

apply a Stockwell transformation (S-Transformation) to the raw signal data in each window to produce an S-transformed data set.

15. The apparatus of claim 14, wherein the signal processor is further configured to apply the Taut-string transformation to the S-transformed data set.

16. The apparatus of claim 14, wherein the raw signal data is electrocardiogram signal data, electroencephalogram data, pulse oximetry waveform data, arterial blood pressure waveform data, venous blood pressure waveform data, intracranial waveform data, or a combination thereof.

17. The apparatus of claim 14, wherein the signal processor is further configured to measure the raw signal data using an electrocardiogram sensor, a respiratory rate sensor, a pulse oximetry sensor, photoplethysmography sensor, inspiration/expiration sensor, arterial blood pressure sensor, and venous blood pressure sensor, impedance sensor, piezoelectric sensor, a Doppler signal, an ultrasound sensor, or intracranial pressure sensor.

18. The apparatus of claim 17, wherein the classification is of hemodynamic decomposition.

19. The apparatus of claim 11, wherein the classification is of hemorrhage, sepsis, cardiogenic shock, stroke, cardiac arrest, brain injury, arrhythmias, heart failure, infection, level of consciousness, and/or a combination thereof.

* * * * *